(12) United States Patent
Kwon et al.

(10) Patent No.: US 9,550,174 B2
(45) Date of Patent: *Jan. 24, 2017

(54) MIXED MANGANESE FERRITE COATED CATALYST, METHOD OF PREPARING THE SAME, AND METHOD OF PREPARING 1,3-BUTADIENE USING THE SAME

(75) Inventors: Yong Tak Kwon, Daejeon (KR); Tae Jin Kim, Daejeon (KR); Young Min Chung, Daejeon (KR); Ok Youn Kim, Daejeon (KR); Seung Hoon Oh, Seoul (KR)

(73) Assignee: SK INNOVATION CO., LTD, Seoul (KR)

( * ) Notice: Subject to any disclaimer, the term of this patent is extended or adjusted under 35 U.S.C. 154(b) by 295 days.

This patent is subject to a terminal disclaimer.

(21) Appl. No.: 13/810,557

(22) PCT Filed: May 26, 2011

(86) PCT No.: PCT/KR2011/003861
§ 371 (c)(1),
(2), (4) Date: Jan. 16, 2013

(87) PCT Pub. No.: WO2012/011659
PCT Pub. Date: Jan. 26, 2012

(65) Prior Publication Data
US 2013/0158325 A1 Jun. 20, 2013

(30) Foreign Application Priority Data
Jul. 20, 2010 (KR) ........................ 10-2010-0069981

(51) Int. Cl.
*B01J 27/224* (2006.01)
*C07C 5/48* (2006.01)
(Continued)

(52) U.S. Cl.
CPC ........... *B01J 27/224* (2013.01); *B01J 23/8892* (2013.01); *B01J 37/0215* (2013.01);
(Continued)

(58) Field of Classification Search
CPC ......... B01J 27/224; B01J 37/03; B01J 37/088; B01J 37/0215; B01J 23/8892; C07C 5/3332; C07C 5/48
See application file for complete search history.

(56) References Cited

U.S. PATENT DOCUMENTS 3,671,606 A 6/1972 Manning
3,743,683 A 7/1973 Gabliks et al.
(Continued)

FOREIGN PATENT DOCUMENTS

JP S47-007920 4/1972
WO 2009028700 A1 3/2009
(Continued)

OTHER PUBLICATIONS

Papa, J.; Marzuka, S.; Brito, J. L.; Guaryan, N. Revista de la Facultad de Ingenieria de la U.C.V., 2006, 21, 101-109.*
(Continued)

*Primary Examiner* — Jun Li
(74) *Attorney, Agent, or Firm* — Abelman, Frayne & Schwab

(57) ABSTRACT

This invention relates to a method of preparing a mixed manganese ferrite coated catalyst, and a method of preparing 1,3-butadiene using the same, and more particularly, to a method of preparing a catalyst by coating a support with mixed manganese ferrite obtained by co-precipitation at 10~40° C. using a binder and to a method of preparing 1,3-butadiene using oxidative dehydrogenation of a crude C4 mixture containing n-butene and n-butane in the presence of the prepared catalyst. This mixed manganese ferrite
(Continued)

coated catalyst has a simple synthetic process, and facilitates control of the generation of heat upon oxidative dehydrogenation and is very highly active in the dehydrogenation of n-butene.

7 Claims, 1 Drawing Sheet

(51) Int. Cl.
| | |
|---|---|
| B01J 23/889 | (2006.01) |
| B01J 37/02 | (2006.01) |
| B01J 37/03 | (2006.01) |
| B01J 37/08 | (2006.01) |
| C07C 5/333 | (2006.01) |

(52) U.S. Cl.
CPC .............. *B01J 37/03* (2013.01); *B01J 37/088* (2013.01); *C07C 5/3332* (2013.01); *C07C 5/48* (2013.01); *C07C 2521/04* (2013.01); *C07C 2521/08* (2013.01); *C07C 2523/34* (2013.01); *C07C 2523/745* (2013.01); *C07C 2523/889* (2013.01); *C07C 2527/224* (2013.01); *Y02P 20/52* (2015.11)

(56) References Cited

U.S. PATENT DOCUMENTS

| | | | |
|---|---|---|---|
| 3,849,545 A | 11/1974 | Miklas | |
| 3,951,869 A * | 4/1976 | Baker | ........................... 502/324 |
| 4,058,577 A | 11/1977 | Baker | |
| 4,347,395 A | 8/1982 | Chu et al. | |
| 4,529,718 A * | 7/1985 | Dupin | ...................... B01J 21/04 |
| | | | 423/628 |
| 4,658,074 A * | 4/1987 | Bajars et al. | ................ 585/380 |
| 5,668,075 A | 9/1997 | Milam et al. | |
| 5,689,023 A | 11/1997 | Hamilton | |
| 2002/0010088 A1* | 1/2002 | Eijsbouts et al. | ............. 502/313 |
| 2004/0133054 A1* | 7/2004 | Pelati et al. | ................... 585/444 |
| 2010/0081855 A1 | 4/2010 | Pelati et al. | |

FOREIGN PATENT DOCUMENTS

| | | | |
|---|---|---|---|
| WO | 2009075478 A2 | | 6/2009 |
| WO | WO2009075478 | * | 6/2009 |

OTHER PUBLICATIONS

Cavani, F. and Trifiro, F. Partial Oxidation of C2 to C4 Paraffins; Baerns, M., Ed.; Basic Principles in Applied Catalysis; Springer-Verlag: Berlin, Germany, 2004, pp. 19-85.*
International Search Report, PCT/KR2011/003861, Feb. 22, 2012, 4 pages.
Office Action in Chinese Patent Application No. 201180036201.1 dated Mar. 5, 2014, 12 pages.
Qiu, Feng-Yan et al., Appl. Catal., 51 (1989) 235-253.
Welch, M. et al., Hydrocarbon Processing, 57(1 1), 131-136 (1978).
Office Action, Jan. 20, 2015, Japanese Patent Application No. 2013-520633.
Office Action, Aug. 30, 2016, Korean Patent Application No. 10-2010-0069981.

* cited by examiner

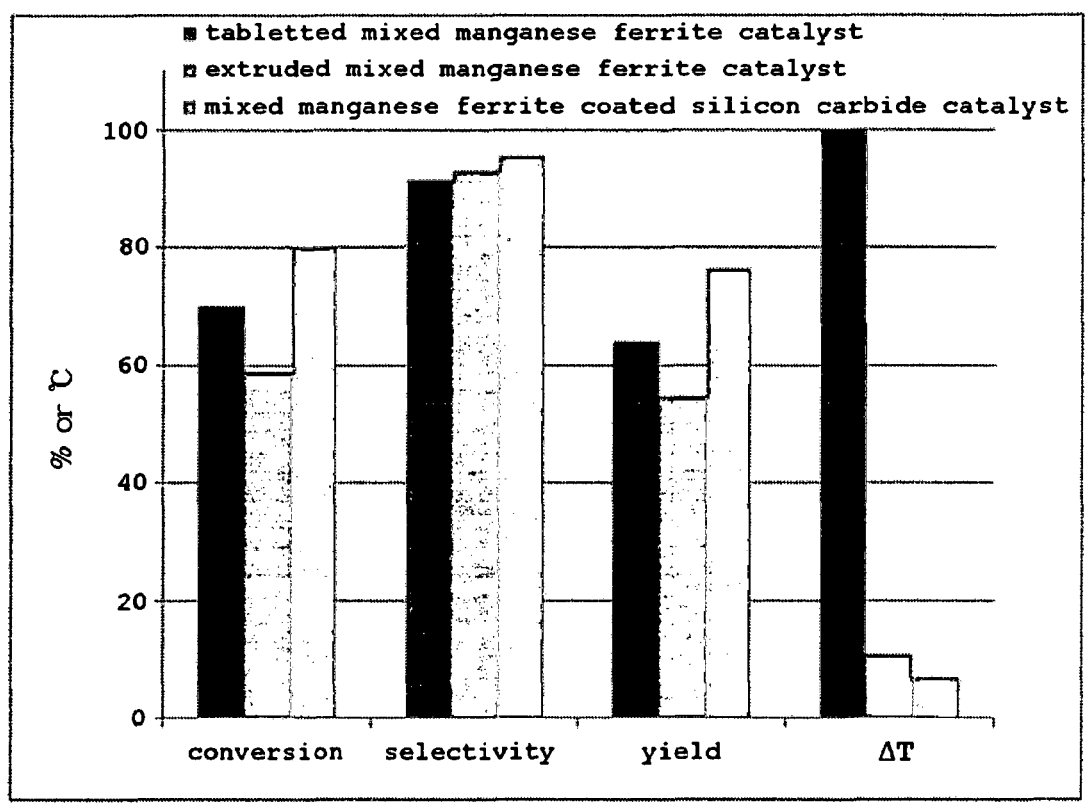

MIXED MANGANESE FERRITE COATED CATALYST, METHOD OF PREPARING THE SAME, AND METHOD OF PREPARING 1,3-BUTADIENE USING THE SAME

RELATED APPLICATIONS

This application is a U.S. national phase application under 35 USC §371 of PCT/KR2011/003861 filed on May 26, 2011, and claims the benefit under 35 USC §119 of Korean patent application number KR 10-2010-0069981 filed Jul. 20, 2010, the disclosures of which are incorporated herein by reference in their entireties.

TECHNICAL FIELD

The present invention relates to a mixed manganese ferrite coated catalyst, a method of preparing the same, and a method of preparing 1,3-butadiene using the same, and, more particularly, to a method of preparing a catalyst comprising coating a support with mixed manganese ferrite obtained by co-precipitation at 10~40° C., with the aid of a binder, and to a method of preparing 1,3-butadiene by oxidative dehydrogenation of an inexpensive crude C4 fraction containing n-butene, n-butane and many other impurities without additionally extracting n-butene, in the presence of the prepared catalyst.

BACKGROUND ART

Oxidative dehydrogenation of n-butene, which is used to produce 1,3-butadiene that is gradually increasing in demand in petrochemical markets, produces 1,3-butadiene and water after reacting n-butene with oxygen, and is thermodynamically favorable because water, which is stable, is produced, and also the reaction temperature may be reduced. If a C4 mixture or C4 raffinate-3 containing impurities such as n-butane is utilized as the supply source of n-butene, the value of surplus C4 fractions may be advantageously increased.

As mentioned above, the oxidative dehydrogenation of n-butene (1-butene, trans-2-butene, cis-2-butene) is a reaction in which 1,3-butadiene and water are produced after a reaction between n-butene and oxygen. Oxidative dehydrogenation, however, is accompanied by many side-reactions, such as complete oxidations, which are expected to occur because oxygen is used as the reactant, and thus the development of catalysts which maximally suppress such side-reactions and increase the selectivity for 1,3-butadiene is regarded as of the utmost importance. The catalysts known to date used in the oxidative dehydrogenation of n-butene include ferrite based catalysts, tin based catalysts, bismuth molybdate based catalysts, etc.

Among these, the ferrite based catalysts have different catalytic activities depending on the kind of metal which occupies divalent cation sites of a spinel structure, and furthermore, zinc ferrite, magnesium ferrite, and manganese ferrite are known to be effective in the oxidative dehydrogenation of n-butene, and zinc ferrite is particularly reported as enabling there to be increased selectivity for 1,3-butadiene compared to when using ferrite catalysts of other metals [F.-Y. Qiu, L.-T. Weng, E. Sham, P. Ruiz, B. Delmon, Appl. Catal., vol. 51, pp. 235 (1989)].

Reported in some patents and pieces of literature is the use of zinc ferrite based catalyst in the oxidative dehydrogenation of n-butene, in which in order to increase the reaction activity and lifetime of the zinc ferrite catalyst used in the oxidative dehydrogenation, pretreatment and post-treatment, including adding an additive to the catalyst, are carried out, so that 1,3-butadiene can be obtained in higher yield over a long period of time [F.-Y. Qiu, L.-T. Weng, E. Sham, P. Ruiz, B. Delmon, Appl. Catal., vol. 51, pp. 235 (1989)/L. J. Crose, L. Bajars, M. Gabliks, U.S. Pat. No. 3,743,683 (1973)/E. J. Miklas, U.S. Pat. No. 3,849,545 (1974)/J. R. Baker, U.S. Pat. No. 3,951,869 (1976)]. In addition to the above zinc ferrite catalyst, the use of manganese ferrite catalyst for oxidative dehydrogenation of n-butene is reported in some patents.

In the oxidative dehydrogenation of n-butene, the zinc ferrite catalyst is problematic because reproducibility may be deteriorated by the addition of metal oxides used in order to prevent inactivation and by the acid treatment, and also complicated post-treatment procedures are required. Further, the manganese ferrite catalyst should be maintained at high temperature upon co-precipitation in order to exist in a pure spinel phase and decreases the yield of 1,3-butadiene compared to when using zinc ferrite.

In addition, the oxidative dehydrogenation of n-butene is problematic because the yield of 1,3-butadiene is lowered when the reactant contains a predetermined amount or more of n-butane [L. M. Welch, L. J. Croce, H. F. Christmann, Hydrocarbon Processing, pp. 131 (1978)]. Thus, in the above conventional techniques, such problems remain unsolved when oxidative dehydrogenation is carried out using only pure n-butene (1-butene or 2-butene) as the reactant. Hence, various pieces of literature or patents related to catalysts and processes for producing 1,3-butadiene from n-butene using oxidative dehydrogenation as above and processes based thereon, including using pure n-butene as the reactant, are disadvantageous because a separation process for extracting pure n-butene from a C4 mixture should be additionally performed, thereby drastically reducing economic efficiency.

DISCLOSURE OF INVENTION

Technical Problem

Accordingly, the present inventors have developed a method of preparing a mixed manganese ferrite catalyst, which enables the catalyst preparation process and the reproducibility of the catalyst preparation to be simple and high and also exhibits high activity for the oxidative dehydrogenation of n-butene in an inexpensive C4 mixture (Korean Patent No. 0888143 (2009)). Although such a mixed manganese ferrite catalyst, which is provided in the form of pellets using tabletting, are highly active in the oxidative dehydrogenation of n-butene in an inexpensive C4 mixture without having to perform additional extraction, it makes it difficult to control the generation of heat during the reaction, undesirably limiting the suppression of side-reactions.

Therefore, an object of the present invention is to provide a method of preparing a mixed manganese ferrite coated catalyst, which is able to control the generation of heat to suppress side-reactions, thus exhibiting very superior catalytic activity so that 1,3-butadiene may be produced in high yield, and also in which the preparation process of the catalyst is simple.

Another object of the present invention is to provide a method of preparing 1,3-butadiene in high yield by performing oxidative dehydrogenation using an inexpensive crude C4 mixture as a reactant in the presence of the catalyst prepared by the above method.

Solution to Problem

In order to accomplish the above objects, an aspect of the present invention provides a method of preparing a mixed manganese ferrite coated catalyst, comprising a) co-precipitating a precursor aqueous solution comprising a manganese precursor and an iron precursor while being mixed in a basic solution, thus forming a co-precipitated solution, b) washing and filtering the co-precipitated solution, thus obtaining a solid sample which is then dried, c) mixing the dried solid sample, a binder and distilled water and an acid at a weight ratio of 1:0.5~2:6~12:0.3~0.8 at room temperature, thus obtaining a mixture, and d) adding a support to the mixture obtained in c) and then performing blending and drying.

Another aspect of the present invention provides a method of preparing 1,3-butadiene, comprising a) supplying, as a reactant, a gas mixture comprising a C4 mixture, air and steam, and b) continuously passing the reactant through a catalyst bed to which the catalyst prepared using the above method is fixed, so that oxidative dehydrogenation is carried out, thus obtaining 1,3-butadiene.

Advantageous Effects of Invention

According to the present invention, when using a catalyst resulting from coating a support having high heat conductivity with mixed manganese ferrite obtained by coprecipitation at 10~40° C. using a binder, it is possible to control the generation of heat to facilitate the suppression of side-reactions, so that 1,3-butadiene can be produced in high yield from an inexpensive C4 mixture containing n-butene and n-butane using oxidative dehydrogenation.

Also, the mixed manganese ferrite coated catalyst which has very simple composition and synthetic route with excellent reproducibility can be obtained. The use of the catalyst prepared according to the present invention facilitates controlling the generation of heat so that a crude C4 mixture containing a high-concentration of n-butane can be used as a reactant for oxidative dehydrogenation without requiring the additional separation of n-butane thus enabling the preparation of 1,3-butadiene, and 1,3-butadiene can be obtained in high yield.

According to the present invention, 1,3-butadiene, which has a high use value in the petrochemical industry, can be prepared from a C4 mixture or C4 raffiante-3 the use value of which is low, thus achieving high added-value of the C4 fractions. Furthermore, an independent production process for preparing 1,3-butadiene can be ensured even without establishing a cracker, thus satisfying the increasing demand for 1,3-butadiene, thereby generating economic benefits, compared to conventional processes.

BRIEF DESCRIPTION OF DRAWINGS

FIG. 1 illustrates the reaction results of Test Example 1 as shown in Table 3 according to the present invention.

MODE FOR THE INVENTION

Hereinafter, a detailed description will be given of the present invention.

The present invention pertains to the preparation of a mixed manganese ferrite coated catalyst for use in the oxidative dehydrogenation of n-butene, by synthesizing mixed manganese ferrite using co-precipitation at 10~40° C., particularly 15~30° C., and then coating a support with the mixed manganese ferrite using a binder, and to a method of preparing 1,3-butadiene via the oxidative dehydrogenation of n-butene using the catalyst thus prepared. As such, 1,3-butadiene can be prepared from a C4 mixture which was not subjected to additional n-butane separation.

The mixed manganese ferrite coated catalyst according to the present invention for preparing 1,3-butadiene in high yield using the oxidative dehydrogenation of n-butene is obtained by coating a support having high heat conductivity with mixed manganese ferrite which is an active material, so that the amount of mixed manganese ferrite per the unit volume of the catalyst is small, thus facilitating control of the generation of heat and exhibiting higher activity and productivity for the oxidative dehydrogenation of n-butene.

A manganese precursor and an iron precursor for synthesizing the manganese ferrite include a chloride precursor or a nitrate precursor, which dissolves well in distilled water which is useful as the solvent. Specifically, the iron precursor is selected from the group consisting of ferrous chloride tetrahydrate, ferrous chloride hexahydrate, ferrous chloride dihydrate, ferric chloride hexahydrate, ferrous nitrate hexahydrate, ferrous nitrate nonahydrate, ferric nitrate hexahydrate, and ferric nitrate nonahydrate.

The manganese precursor is selected from the group consisting of manganous chloride, manganous chloride tetrahydrate, manganic chloride, manganese tetrachloride, manganese nitrate hexahydrate, manganese nitrate tetrahydrate, and manganese nitrate monohydrate.

The amounts of the manganese precursor and the iron precursor are adjusted so that the atom ratio of iron/manganese is 2.0~2.5, and these precursors in such amounts are respectively dissolved in distilled water, and then mixed together. If the atom ratio of iron/manganese falls outside of 2.0~2.5, manganese is difficult to interpose into iron lattices, or the activity of the catalyst decreases drastically.

In order to co-precipitate the manganese precursor and the iron precursor at room temperature, a 1.5~4 M basic solution, for example, a 3 M sodium hydroxide aqueous solution, is separately prepared. If the concentration of the basic solution is less than 1.5 M, it is difficult to form a mixed manganese ferrite catalyst structure. In contrast, if the concentration thereof is higher than 4 M, in the case of a metal ion combined with a hydroxyl group, for example, sodium hydroxide, it is difficult to remove a Na ion upon washing, undesirably decreasing the activity. The case where the molar concentration of the basic solution is adjusted to within the range of 2~3 M is useful in terms of forming a mixed manganese ferrite structure and performing post-treatment. The basic solution used for co-precipitating the manganese precursor and the iron precursor may include another type of basic solution including ammonia water, in addition to sodium hydroxide. The pH of the basic solution may fall in the range of 9~14.

To obtain the mixed manganese ferrite from the manganese precursor and the iron precursor, the aqueous solution in which the manganese precursor and the iron precursor were dissolved is introduced into the basic solution at 10~40° C. Stirring is performed for 2~12 hours, in particular 6~12 hours so that the introduction rate is maintained uniform and sufficient co-precipitation takes place.

If the co-precipitation is carried out at a temperature lower than 10° C., it becomes insufficient thus forming very unstable bonds, undesirably causing side-reactions which are difficult to control upon using a catalyst. If the temperature is higher than 40° C., the catalytic activity may deteriorate. The co-precipitation may be carried out at 15~30° C., particularly 15~25° C.

The stirred co-precipitation solution is phase separated for a sufficient period of time so that the solid catalyst precipitates, after which washing and filtering under reduced pressure are performed, after which a precipitated solid sample is obtained.

The solid sample thus obtained is dried at 70~200° C., particularly 120~180° C. for 24 hours, thus preparing mixed manganese ferrite.

The binder used to coat a support with the dried mixed manganese ferrite may include alumina having a specific surface area of 70~250 m$^2$/g. This alumina may use boehmite or alumina sol as a precursor, and boehmite is particularly useful.

In the coating of the support with the mixed manganese ferrite, an acid is added to gel boehmite, and may be selected from the group consisting of nitric acid, hydrochloric acid, sulfuric acid, phosphoric acid, and acetic acid.

The support which will be coated with the mixed manganese ferrite may be selected from the group consisting of silicon carbide, alumina or silica. Particularly useful is silicon carbide. The size and the shape of the support may vary depending on the size of a reactor used for the reaction, and are not limited but a spherical or cylindrical support having a size of 1~10 mm may be used.

The mixed manganese ferrite, boehmite, distilled water and nitric acid are mixed at a weight ratio of 1:0.5~2:6~12: 0.3~0.8, particularly 1:1~1.5:8~10:0.4~0.6. To this mixture, the support is added in an amount 5~15 times, particularly 10~12 times the weight of mixed manganese ferrite, and blended using a roll mixer and dried at 50~80° C., thus obtaining a mixed manganese ferrite coated catalyst.

The dried mixed manganese ferrite coated catalyst is placed in an electric furnace and heat treated at 350~800° C., particularly 500~700° C.

In the present invention, the X-ray diffraction peaks of the mixed manganese ferrite used as the active material have the 2-theta range of 18.78~18.82, 24.18~24.22, 33.2~33.24, 35.64~35.68, 40.9~40.94, 45.22~45.26, 49.56~49.6, 54.22~54.26, 55.24~55.28, 57.92~57.96, 62.56~62.6, 64.04~64.08, 66.02~66.06, 72.16~72.2, and 75.78~75.82. The most remarkable peak is observed in the 2-theta range of 33.2~33.24.

In addition, the present invention provides a method of preparing 1,3-butadiene using a C4 mixture, which was not subjected to additional n-butane separation, as the supply source of n-butene via oxidative dehydrogenation in the presence of the mixed manganese ferrite coated catalyst which was co-precipitated at room temperature. The C4 mixture is selected from the group consisting of 1-butene, 2-butene, and C4 raffinates-1, 2, 2.5, 3.

In Test Example 1 according to the present invention, a powder of the catalyst is fixed to a straight type stainless steel reactor for the catalytic reaction, and the reactor is placed in an electric furnace so that the reaction temperature of the catalyst bed is maintained constant, after which the reactants are reacted while continuously passing through the catalyst bed of the reactor.

The reaction temperature for oxidative dehydrogenation is maintained at 300~600° C., particularly 350~500° C., more particularly 400° C. The amount of the catalyst is set so that the WHSV (Weight Hourly Space Velocity) as the flow rate of reactants, is 1~5 h$^{-1}$, particularly 2~3 h$^{-1}$, more particularly 2.5 h$^{-1}$, based on n-butene. The reactants include the C4 mixture and the air and the steam at a ratio of 1:0.5~10:1~50, particularly 1:2~4:10~30. If the mixing ratio of the gas mixture falls outside of the above range, a desired butadiene yield cannot be obtained, or problems may occur due to drastic heat generation when the reactor is operated.

In the present invention, n-butene and oxygen which are reactants for the oxidative dehydrogenation are supplied in the form of a gas mixture, and the amounts of the C4 mixture or the C4 raffinate-3 which is the supply source of n-butene and the air which is another reactant are precisely controlled and supplied using a piston pump and a mass flow rate regulator, respectively. In order to supply steam which is known to alleviate the reaction heat of oxidative dehydrogenation and to increase the selectivity for 1,3-butadiene, water in a liquid phase is gasified while being introduced using a mass flow rate regulator, so that the steam is supplied into the reactor. The temperature near the inlet through which the water is introduced is maintained at 300~450° C., particularly 350~450° C., whereby the introduced water is instantly gasified and mixed with other reactants (C4 mixture and air), and then passes through the catalyst bed.

Among the reactants which react in the presence of the catalyst according to the present invention, the C4 mixture includes 0.5~50 wt % of n-butane, 40~99 wt % of n-butene, and 0.5~10 wt % of a C4 admixture which does not contain any n-butane and n-butene. The C4 admixture without the n-butane and n-butene includes for example isobutene, cyclobutane, methyl cyclopropane, isobutene, etc.

When an inexpensive C4 mixture or C4 raffinate-3, including n-butene, is subjected to oxidative dehydrogenation using the mixed manganese ferrite coated catalyst according to the present invention, 1,3-butadiene can be produced in high yield from n-butene contained in the reactant.

Also when the support is used in the form of being coated with the mixed manganese ferrite in the present invention, the amount of mixed manganese ferrite which is the active material per the unit volume of the catalyst is small thus making it easy to control the generation of heat upon oxidative dehydrogenation, and the composition and the synthetic route of the catalyst are simple, advantageously ensuring reproducibility.

A better understanding of the present invention may be obtained in light of the following examples which are set forth to illustrate, but are not to be construed as limiting the present invention.

Preparative Example 1

Preparation of Tabletted Mixed Manganese Ferrite Catalyst

In order to prepare a tabletted mixed manganese ferrite catalyst, manganese chloride tetrahydrate ($MnCl_2.4H_2O$) as a manganese precursor, and iron chloride hexahydrate ($FeCl_3.6H_2O$) as an iron precursor were used, both of which were well dissolved in distilled water. 198 g of manganese chloride tetrahydrate and 541 g of iron chloride hexahydrate were dissolved in distilled water (1000 ml), mixed and stirred. After sufficient stirring, the complete dissolution of precursors was confirmed, and the precursor aqueous solution was added in droplets to a 3 M sodium hydroxide aqueous solution (6000 ml) at 20° C. at a predetermined rate. This mixture solution was stirred at room temperature for 12 hours using a stirrer so as to be sufficiently stirred, and then allowed to stand at room temperature for 12 hours so as to achieve phase separation. The precipitated solution was washed with a sufficient amount of distilled water, and filtered using a filter under reduced pressure thus obtaining a solid sample which was then dried at 160° C. for 24 hours.

The produced solid sample was heat treated in an electric furnace at 650° C. in an air atmosphere for 3 hours, thereby preparing a manganese ferrite catalyst having a mixed phase. The prepared catalyst phase was analyzed using X-ray diffraction under the following conditions. The results are shown in Table 1 below. As shown in Table 1, the catalyst prepared at room temperature was confirmed to be mixed manganese ferrite containing iron oxide ($\alpha$-$Fe_2O_3$) and manganese iron oxide ($MnFeO_3$). In order to evaluate the activity thereof, the completed mixed manganese ferrite catalyst was prepared into pellets using tabletting, and milled to a size of 0.9~1.2 mm.

<Conditions for X-ray Diffraction>
X-ray generator: 3 kW, Cu—K$\alpha$ ray ($\lambda$=1.54056 Å)
Tube voltage: 40 kV
Tube current: 40 mA
2-theta measurement range: 5 deg~90 deg
Sampling width: 0.02 deg
Injection rate: 5 deg 2-theta/min
Divergence slit: 1 deg
Scattering slit: 1 deg
Receiving slit: 0.15 mm

TABLE 1

X-ray Diffraction Results of Mixed Manganese Ferrite Catalyst

| 2-Theta | |
|---|---|
| 18.8 | $MnFeO_3$ |
| 24.2 | $\alpha$-$Fe_2O_3$ |
| 33.22 | $MnFeO_3$ |
| 35.66 | $MnFe_2O_4$ |
| 40.92 | $MnFeO_3$ |
| 45.24 | $MnFeO_3$ |
| 49.58 | $MnFeO_3$ |
| 54.24 | $\alpha$-$Fe_2O_3$ |
| 55.26 | $MnFeO_3$ |
| 57.94 | $MnFe_2O_4$ |
| 62.58 | $MnFe_2O_4$ |
| 64.06 | $MnFeO_3$ |
| 66.04 | $\alpha$-$Fe_2O_3$ |
| 72.18 | $MnFe_2O_4$ |
| 75.8 | $MnFe_2O_4$ |

Preparative Example 2

Preparation of Extruded Mixed Manganese Ferrite Catalyst

Before the heat treatment was performed in Preparative Example 1, 5 g of dried mixed manganese ferrite, 50 g of boehmite, 30 g of distilled water, and 3 g of nitric acid (60%) were mixed at room temperature. This mixture was placed into an extruder and extruded into a cylindrical form (diameter: 1 mm, length: 10 cm). The extruded mixed manganese ferrite catalyst was placed in an electric furnace, dried at 120° C. for 2 hours, and then heat treated at 650° C. for 3 hours, thus completing a catalyst. The completed catalyst was milled to a size of 0.9~1.2 mm as in Preparative Example 1.

Preparative Example 3

Preparation of Mixed Manganese Ferrite Coated Silicon Carbide Catalyst

Before the heat treatment was performed in Preparative Example 1, 5 g of dried mixed manganese ferrite, 5 g of boehmite, 50 g of distilled water, and 3 g of nitric acid (60%) were mixed at room temperature. This mixture was added with 50 g of spherical silicon carbide having a diameter of 1 mm, and blended using a roll mixer and dried at 60° C. The dried mixed manganese ferrite coated silicon carbide catalyst was placed in an electric furnace, and then heat treated at 650° C. for 3 hours, thus completing a catalyst.

Example 1

Oxidative Dehydrogenation of C4 Raffinate-3 or C4 Mixture Using Mixed Manganese Ferrite Coated Silicon Carbide Catalyst Using the mixed manganese ferrite coated silicon carbide catalyst of Preparative Example 3, oxidative dehydrogenation of n-butene was carried out. The specific reaction conditions are described below.

The reactant used for the oxidative dehydrogenation of n-butene was a C4 mixture. The composition thereof is shown in Table 2 below. The C4 mixture was supplied in the form of a gas mixture along with air and steam, and a straight type fixed-bed reactor made of stainless steel was used.

The ratio of reactants was set based on n-butene in the C4 mixture, so that the ratio of n-butene:air:steam was 1:3:20. The steam was obtained by gasifying water in a liquid phase at 350° C., mixed with the other reactants including C4 mixture and air, and then fed into the reactor. The amount of C4 mixture was controlled using a pump, and the amounts of air and steam were regulated using a mass flow rate regulator.

The amount of the catalyst was set so that the WHSV as the flow rate of the reactants was 2.5 $h^{-1}$ based on n-butene in the C4 mixture. The reaction temperature was maintained so that the temperature of the catalyst bed of the fixed-bed reactor was 400° C. The reaction product was composed of, in addition to the desired 1,3-butadiene, carbon dioxide which is a byproduct of complete oxidation, a cracking byproduct, and an isomerization byproduct, and n-butane contained in the reactant, and was separated and analyzed using gas chromatography. When using the mixed manganese ferrite catalyst for oxidative dehydrogenation of n-butene, the conversion of n-butene, and the selectivity and yield of 1,3-butadiene were calculated according to Equations 1, 2 and 3 below.

$$\text{Conversion (\%)} = \frac{\text{moles of reacted } n\text{-butene}}{\text{moles of fed } n\text{-butene}} \times 100 \quad \text{Equation 1}$$

$$\text{Selectivity (\%)} = \frac{\text{moles of produced 1,3-butadiene}}{\text{moles of reacted } n\text{-butene}} \times 100 \quad \text{Equation 2}$$

$$\text{Yield (\%)} = \frac{\text{moles of produced 1,3-butadiene}}{\text{moles of fed } n\text{-butene}} \times 100 \quad \text{Equation 3}$$

TABLE 2

Composition of C4 Mixture used as Reactant

| Composition | Molecular Formula | Weight % |
|---|---|---|
| i-Butane | $C_4H_{10}$ | 0 |
| n-Butane | $C_4H_{10}$ | 26.8 |
| Methyl Cyclopropane | $C_4H_8$ | 0.1 |
| trans-2-Butene | $C_4H_8$ | 44.1 |
| Butene-1 | $C_4H_8$ | 6.6 |
| Isobutylene | $C_4H_8$ | 0 |
| cis-2-Butene | $C_4H_8$ | 21.9 |
| Cyclobutane | $C_4H_8$ | 0.5 |
| i-Pentane | $C_5H_{12}$ | 0 |
| Total | | 100 |

Test Example 1

Reaction Activities of Mixed Manganese Ferrite Coated Silicon Carbide Catalyst, Extruded Mixed Manganese Ferrite Catalyst and Tabletted Mixed Manganese Ferrite Catalyst The catalysts of Preparative Examples 1~3 were applied to the oxidative dehydrogenation of a C4 mixture according to the reaction of Example 1. The results are shown in Table 3 below and FIG. 1. The case where the mixed manganese ferrite coated silicon carbide catalyst was used could result in an 80% conversion of n-butene, a 95.5% selectivity for 1,3-butadiene, a 76.4% yield of 1,3-butadiene, and also changes in temperature of the catalyst bed were 10° C. or less, from which the generation of heat was evaluated to have been efficiently controlled.

TABLE 3

| Preparative Example | n-Butene Conversion (%) | 1,3-Butadiene Selectivity (%) | 1,3-Butadiene Yield (%) | ΔT (° C.) |
|---|---|---|---|---|
| 1* | 70 | 91.5 | 64.1 | 100 |
| 2* | 59 | 92.8 | 54.8 | 11 |
| 3 | 80 | 95.5 | 76.4 | 7 |

*Comparative Preparative Example

As is apparent from Table 3, the extruded mixed manganese ferrite catalyst had low changes in temperature, but exhibited comparatively low conversion and yield because of the small number of active sites of the mixed manganese ferrite exposed so as to function efficiently as an actual catalyst.

In the case of the mixed manganese ferrite coated silicon carbide catalyst obtained by coating silicon carbide having a small specific surface area and a small pore volume with mixed manganese ferrite, the mixed manganese ferrite that is the active material is entirely exposed near the surface of the catalyst and thus can exclusively function as the active sites of the catalyst. Whereas, in the case of the extruded catalyst, active sites are combined with alumina having a large specific surface area and a large pore volume and are present not only on the surface of the catalyst but also in the pores and thus are not exposed and cannot act as active sites. Even when extrusion is performed using manganese ferrite of the same amount, the activity is not exhibited as in the coated catalyst. Therefore, the mixed manganese ferrite coated silicon carbide catalyst can manifest higher conversion or selectivity and can very efficiently control the generation of heat, compared to the mixed manganese ferrite catalysts of comparative preparative examples.

Although the embodiments of the present invention have been disclosed for illustrative purposes, those skilled in the art will appreciate that a variety of different modifications, additions and substitutions are possible, without departing from the scope and spirit of the invention as disclosed in the accompanying claims. Accordingly, such modifications, additions and substitutions should also be understood as falling within the scope of the present invention.

The invention claimed is:

1. A method of preparing a mixed manganese ferrite coated catalyst for use in preparing 1,3-butadiene, comprising:
 a) co-precipitating a precursor aqueous solution comprising a manganese precursor and an iron precursor while being mixed in a basic solution, thus forming a co-precipitated solution;
 b) washing and filtering the co-precipitated solution, thus obtaining a solid sample of mixed manganese ferrite which is then dried at 70~200° C.;
 c) mixing the dried solid sample of mixed manganese ferrite, a binder of alumina, distilled water and an acid at a weight ratio of 1:1~1,5: 8~10:0.4~0.6 at room temperature, thus obtaining a mixture, wherein said alumina is boehmite and the acid is selected from the group consisting of nitric acid, sulfuric acid, hydrochloric acid and phosphoric acid; and
 d) adding a support to the mixture obtained in c) and then performing blending and drying, wherein said drying is performed at 50~80° C., and the support is silicon carbide.

2. The method of claim 1, wherein amounts of the manganese precursor and the iron precursor are adjusted so that an atom ratio of iron/manganese is 2.0~2.5.

3. The method of claim 1, wherein the precursor aqueous solution is co-precipitated while being mixed in a 1.5~4,0 M basic solution at 10~40° C.

4. The method of claim 1, further comprising heat treating the solid catalyst dried in d) at 350~800° C.

5. The method of claim 1, wherein the support is a spherical or cylindrical support having a size of 1~10 mm.

6. The method of claim 1, wherein the support is used in an amount 5~15times the weight of the dried solid sample.

7. The method of claim 1, wherein the alumina has a specific surface area of 70~250m$^2$/g.

* * * * *